United States Patent [19]
Gibbs et al.

[11] Patent Number: 5,330,482
[45] Date of Patent: Jul. 19, 1994

[54] ENDOSCOPIC EXTRACTION DEVICES, WIRE BASKET STONE EXTRACTORS, STENT RETRIEVERS, SNARES AND METHOD OF CONSTRUCTING THE SAME

[75] Inventors: Rebecca C. Gibbs, Greensboro; Mark C. Martel, Winston-Salem, both of N.C.; Zdenek A. Fremund, Montvale, N.J.

[73] Assignee: Wilson-Cook Medical Inc., Winston-Salem, N.C.

[21] Appl. No.: 127,446

[22] Filed: Sep. 27, 1993

Related U.S. Application Data

[63] Continuation of Ser. No. 715,987, Jun. 17, 1991, abandoned.

[51] Int. Cl.$^5$ .................... A61B 17/22; A61B 17/50
[52] U.S. Cl. ..................... 606/113; 606/106; 606/127; 228/262.31; 428/660; 428/685
[58] Field of Search .............. 606/78, 106, 113, 127, 606/128, 108; 228/262.31; 428/960, 660, 680, 685, 679

[56] References Cited

U.S. PATENT DOCUMENTS

| | | | |
|---|---|---|---|
| 5,018,969 | 5/1991 | Andreiko et al. | |
| 5,064,428 | 11/1991 | Cope et al. | 606/127 |
| 5,098,441 | 3/1992 | Wechler | 606/113 |
| 5,171,233 | 12/1992 | Amplatz et al. | 606/127 X |

Primary Examiner—Michael H. Thaler
Attorney, Agent, or Firm—Woodard, Emhardt, Naughton, Moriarty & McNett

[57] ABSTRACT

Disclosed herein is an endoscopic extraction device which retains its operative usefulness for longer periods of time, and therefore need to be replaced less frequently. This extended instrument life is accomplished through the use of a composite wire construction, which includes, an inner monofilament wire of nitinol material surrounded by six stranded stainless steel wires. A wire construction in which a nitinol wire is surrounded by five stranded stainless steel wires is also disclosed. After constructing a wire basket in the normal manner using this material, heat is applied to the formed basket in its pre-formed shape to set the memory characteristics of the inner nitinol core.

23 Claims, 2 Drawing Sheets

ENDOSCOPIC EXTRACTION DEVICES, WIRE BASKET STONE EXTRACTORS, STENT RETRIEVERS, SNARES AND METHOD OF CONSTRUCTING THE SAME

This application is a continuation of application Ser. No. 07/715,987 filed Jun. 17, 1991, now abandoned.

BACKGROUND OF THE INVENTION

1. Field of the Invention

The field of this invention is medical extraction devices, particularly such devices which are used to endoscopically remove foreign bodies from a patient.

2. Description of the Prior Art

In the medical field of gastroenterology, extraction devices are commonly used to endoscopically incise and/or grasp and remove foreign bodies from a patient. For example, a wire basket stone extractor might be used to extract gallstones from the bile duct of a patient. In such an operation, the stone extractor would be advanced through an endoscope, with its wire basket retracted within a retaining cannula. Once advanced, the wire basket would then be extended out of the retaining cannula, with the basket wires opening up into their pre-formed basket configuration. The basket is then manipulated to grasp and remove the gallstones from the patient.

The wire material used in prior art wire basket stone extractors and the like has most commonly been either monofilament or stranded stainless steel wire, and has generally been found to be satisfactory for the purpose intended. The stainless steel wire retains its pre-formed orientation, and returns to its basket configuration when extended from its retaining cannula, even after repeated use. After extended periods of non-use or after long-term repeated use, however, these wire baskets slowly tend to lose their pre-formed orientation, and eventually need to be replaced. The medical art in this area would benefit from an improved extraction device which holds its designed orientation longer and more precisely, and which therefore has to be replaced less frequently.

SUMMARY OF THE INVENTION

The present invention makes available to the medical practitioner endoscopic extraction devices which retain their operative usefulness for longer periods of time, and therefore need to be replaced less frequently. This extended instrument life is accomplished through the use of a composite wire construction, which includes, according to one embodiment, an inner monofilament wire of nitinol material surrounded by six stranded stainless steel wires. In a second disclosed embodiment, the inner nitinol wire is surrounded by five stranded stainless steel wires. After constructing, for example, a wire basket in the normal manner using this material, heat is applied to the formed basket in its pre-formed shape to set the memory characteristics of the inner nitinol core. The result is a durable wire basket which is easy to construct and which maintains its operative usefulness, even after continuous repeated use over long periods of time, or after extended periods of non-use.

BRIEF DESCRIPTION OF THE DRAWINGS

FIG. 1b shows a cross-sectioned view of the composite construction illustrated in FIG. 1a.

FIG. 1b shows a cross-sectioned view of the composite construction illustrated in FIG. 1a.

DESCRIPTION OF THE PREFERRED EMBODIMENT

Figure 1B:
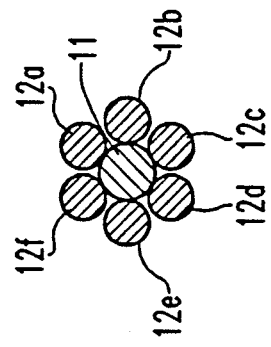
Figure 2B:
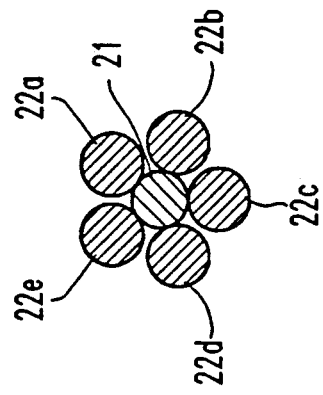
FIG. 2a is schematical view of a 1×6 stranding configuration used in the present invention, wherein a central wire of nitinol material is surrounded by five stranded stainless steel wires.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1A:
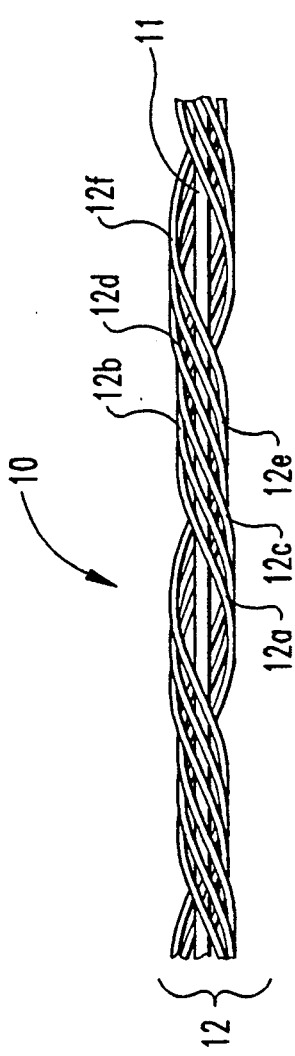
FIG. 1a is schematical view of a 1×7 stranding configuration used in the present invention, wherein a central wire of nitinol material is surrounded by six stranded stainless steel wires.

Referring now to the drawings, FIG. 1a is schematical view of an extraction wire 10 formed in a 1×7 configuration, wherein a central wire 11 of nitinol material is surrounded by stranding 12 of six stranded stainless steel wires 12a-f. The spacing between wiring, as shown by the FIG. 1a, is for illustration purposes to show the relative orientation of the wiring, and does not occur in extraction wire 10, as actually constructed. The stranded construction of extraction wire 10 has a right hand lay 0.053". Inner wire 11 has a diameter of 0.005" and surrounding wires 12a-f each have a diameter of 0.004". The overall diameter of extraction wire 10 is 0.013". FIG. 1b shows a cross-sectioned view of the composite construction of extraction wire 10.

Figure 2A:
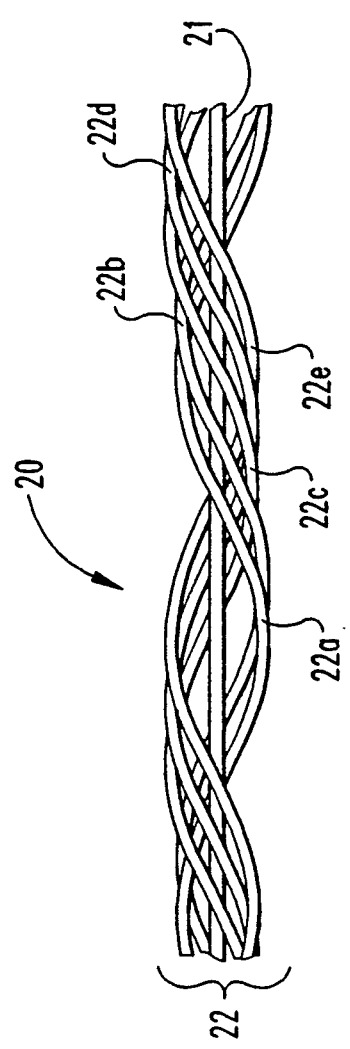

FIG. 2a is schematical view of a second extraction wire 20 formed in a 1×6 configuration, wherein a central wire 21 of nitinol material is surrounded by a stranding 22 of five stainless steel wires 22a-e. As with FIG. 1a, the spacing between wiring shown by the FIG. 2a is for illustration purposes to show the relative orientation of the wiring, and does not occur in the actually constructed extraction wire 20. The construction of extraction wire 20 has a right hand lay of 0.082". Inner wire 21 has a diameter of 0.005" and surrounding wires 22a-e each have a diameter of 0.055". The overall diameter of extraction wire 20 is 0.017". FIG. 1b shows a cross-sectioned view of the composite construction of extraction wire 20.

Figure 3:
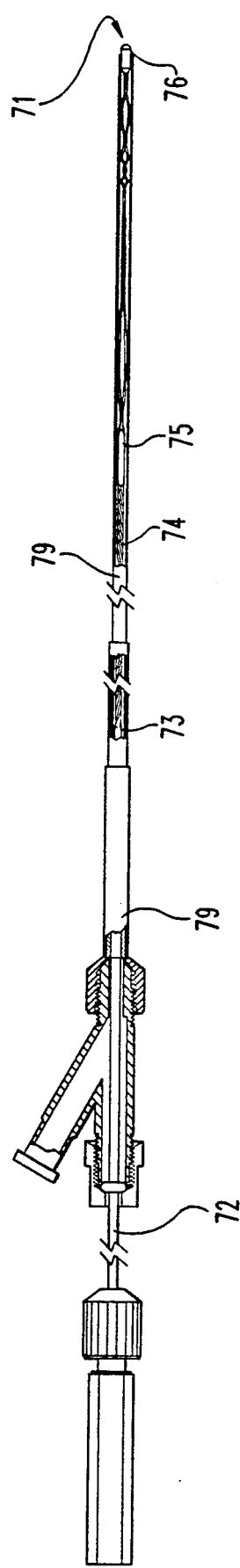
FIG. 3 is a partial fragmentary and partially cross-sectioned illustration of a wire basket stone extractor according to the present invention, with wire basket 77 retained within retaining cannula 79.
Figure 4:
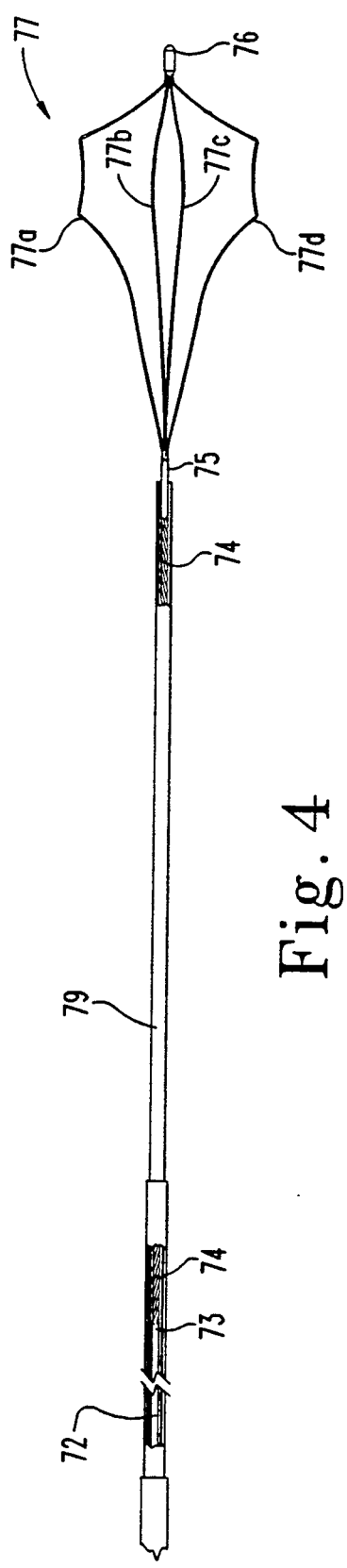
FIG. 4 is a illustration of the wire basket stone extractor of FIG. 3, with wire basket 77 extended out from retaining cannula 79 and into its preformed basket configuration.

FIGS. 3 and 4, in combination, show the operation of a wire basket stone extractor made according to the present invention. FIG. 3 is a partial fragmentary and partially cross-sectioned illustration of a wire basket stone extractor 70, which includes wire basket assembly 71 and retaining cannula 79. Wire basket assembly 71 includes push rod 72, pushrod/cable solder joint 73, cable 74, proximal basket hub solder joint 75, distal basket hub solder joint 76, and extraction wires 77a-d.

Extraction wires 77a–d are made of the composite construction shown for wire 10 in FIGS. 1a–b, and each include a central wire 11 of nitinol surrounded by a stranding 12 of six stainless steel wires 12a–b, as shown and described in relation to wire 10 in FIG. 3, wire basket assembly 71 is shown in its retracted position in relation to retaining cannula 79, with wire basket 77 being held within, and being retained in a collapsed condition by, retaining cannula 79. FIG. 4 illustrates the wire basket stone extractor 70 of FIG. 3, with wire basket 77 extending out from retaining cannula 79 and into its preformed basket configuration for its intended operative purpose. This is accomplished by pushing push rod 72, which movement projects wire basket 77 distally out of retaining cannula 79, allowing wire basket 77 to assume its preformed shape.

The method of construction of wire basket stone extractor 70 will now be discussed with reference to the elements of wire basket stone extractor 70 shown in FIGS. 3 and 4 and the extraction wire construction shown in FIGS. 1a–b. Extraction wires 77a–d are constructed of approximately equal length out of a composite construction which includes an inner monofilament wire 11 of shape memory material (nitinol) surrounded by a stranding 12 of a six stainless steel wires 12a–f. Extraction wires are joined by soldering stainless steel strands 12 together at one end at push rod/cable solder joint 73 and attached to push rod 72 at joint 73. At the distal end, extraction wires 77a–d are also joined by soldering at stainless steel strands 12 together at distal basket hub soldering joint 76. Extraction wires 77a–d are then also joined at a set position a set distance from the distal end of extraction wires 77a–d by soldering stainless steel strands 12 together at proximal basket hub solder joint 75.

Wire basket 77 may then be formed by separating extraction wires 77a–d from each other in the area between proximal basket hub soldering joint 75 and distal basket hub soldering joint 76, and bending extraction wires 77a–d into a desired configuration for use, as shown in FIG. 4. The remaining portion of extraction wires 77a–d between joints 74 and 75 are stranded together to form cable 74. After wire basket 77 has been formed, heat is applied to wire basket 77 to set the shape memory characteristics of inner monofilament wires 11. After cooling, wire basket assembly 71 may then be placed in retaining cannula 79 to complete the assembly of extractor 70.

The shape memory material used in extraction wires 10 and 20 is a nickel titanium alloy known as nitinol, which is composed of about 55% Ni and 44% Ti, with trace elements of Cu (150 ppm), Fe (110 ppm), and Mn (21 ppm). As a shape memory material, nitinol central wires 11 and 21 have the characteristic of superelasticity whereby they exhibit a superelastic tendency to retain the shape in which they are formed when heat is applied to a suitable presorting temperature. This characteristic serves to reinforce the orientation toward the configuration into which extraction wires constructed in this manner are bent to form a wire basket or other extracting configuration, such as a snare. The use of the composite construction with a nitinol inner core and surrounding stainless steel strands, as described herein, allows for ease of construction in that the surrounding stainless steel strands 12 and 22 can easily be soldered to each other at joints 73, 75, and 76, whereas nitinol material is not nearly so readily joinable. In addition to the improvements in efficiency of construction and enhanced durability and reliability of operation, the use of the described composite construction also provides a savings in cost of material over the use of a single superelastic material for the forming of extraction wires.

It is to be noted that, while two specific examples of extraction wire construction have been disclosed herein, other configurations are suitable which fall within the scope of this invention. Also, while stainless steel is particularly suited for strands 12 and 22, other materials which are readily joinable relative to shape memory material may satisfactorily serve in an alternative construction. And it is to be further noted that while an example as been provided in which the present invention has been incorporated into a four wire basket, there are many other extraction configurations for wire baskets, stent retrievers, snares etc. in which the present invention is useful. Therefore, while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. In a medical extraction device, said device including a retaining cannula and an extraction assembly including at least one extraction wire extendable from said retaining cannula into a pre-formed configuration for removing a foreign body from within a patient, the improvement comprising said extraction wire being constructed out of a composite construction which includes an inner monofilament wire of shape memory material surrounded by a plurality of at least five outer stranded wires stranded together about said inner monofilament wire of shape memory material, said outer stranded wires being made of material which is readily solderable as compared to said shape memory material, and wherein said extraction wire is attached to the rest of said extraction assembly by the soldering of said outer stranded wires to each other and to the rest of said extraction assembly.

2. The improvement in a medical extraction device according to claim 1 in which said stranded wires are made of stainless steel.

3. The improvement in a medical extraction device according to claim 2 in which said stranded stainless steel wires includes five wires.

4. The improvement in a medical extraction device according to claim 2 in which said stranded stainless steel wires includes six wires.

5. The improvement in a medical extraction device according to claim 1 in which said shape memory material is nitinol.

6. The improvement in a medical extraction device according to claim 4 in which said shape memory material is nitinol.

7. The improvement in a medical extraction device according to claim 5 in which said shape memory material is nitinol.

8. The improvement in a medical extraction device according to claim 6 in which said inner wire has a diameter of about 0.005" and said surrounding wires each have a diameter of about 0.0055".

9. The improvement in a medical extraction device according to claim 7 in which said inner wire has a diameter of about 0.005" and said surrounding wires each have a diameter of about 0.0004".

10. An improvement in the method for constructing a medical extraction device, said medical extraction device including a retaining cannula, and an extraction assembly including at least one extraction wire extendable from said retaining cannula into a pre-formed configuration for removing a foreign body from within a patient, the improvement comprising the steps of:

constructing said extraction wire out of a composite construction which includes an inner monofilament wire of shape memory material surrounded by a plurality of at least five outer stranded wires stranded together about said inner monofilament wire of shape memory material, said outer stranded wires being made from a material which is readily solderable as compared to said shape memory material;

joining said extraction wire to the rest of said extraction assembly by soldering said stranded wires to each other and to the rest of said extraction assembly;

forming said extraction wire into a desired configuration for use in said medical extraction device; and applying heat to said formed extraction wire to set the shape memory characteristics of said inner monofilament wire of shape memory material.

11. The improvement in the method for constructing a medical extraction device according to claim 10 in which said stranded wires are made of stainless steel.

12. The improvement in the method for constructing a medical extraction device according to claim 10 in which said shape memory material is nitinol.

13. The improvement in the method for constructing a medical extraction device according to claim 11 in which said stranded stainless steel wires includes five wires.

14. The improvement in the method for constructing a medical extraction device according to claim 11 in which said stranded stainless steel wires includes six wires.

15. The improvement in the method for constructing a medical extraction device according to claim 13 in which said shape memory material is nitinol.

16. The improvement in the method for constructing a medical extraction device according to claim 14 in which said shape memory material is nitinol.

17. The improvement in the method for constructing a medical extraction device according to claim 15 in which said inner wire has a diameter of about 0.005" and said surrounding wires each have a diameter of about 0.0055".

18. The improvement in the method for constructing a medical extraction device according to claim 16 in which said inner wire has a diameter of about 0.005" and said surrounding wires each have a diameter of about 0.0004".

19. An improvement in the method for constructing a medical extraction device, said medical extraction device including a retaining cannula and an extraction assembly including a plurality of extraction wires extendable from said retaining cannula into a pre-formed configuration for removing a foreign body from within a patient, the improvement comprising the steps of:

constructing a plurality of extraction wires of approximately equal length out of a composite construction which includes an inner monofiliment wire of shape memory material surrounded by a plurality of at least five outer stranded wires stranded together about said inner monofilament wire of shape memory material, said outer stranded wires being made of material which is readily solderable as compared to said shape memory material;

joining the ends of said extraction wires by soldering said outer standard wires together at said ends;

joining said extraction wires at a set position a set distance from the distal end of said extraction wires by soldering said outer stranded wires together at said set position;

forming said extraction wires in the area between said set position and the distal end of said extraction wires into a desired configuration for use in said medical extraction device; and applying heat to said formed extraction wires to set the shape memory characteristics of said inner monofilament wire of shape memory material.

20. The improvement in the method for constructing a medical extraction device according to claim 19 in which said stranded wires are made of stainless steel.

21. The improvement in the method for constructing a medical extraction device according to claim 20 in which said stranded stainless steel wires includes five wires.

22. The improvement in the method for constructing a medical extraction device according to claim 20 in which said stranded stainless steel wires includes six wires.

23. The improvement in the method for constructing a medical extraction device according to claim 19 in which said shape memory material is nitinol.

* * * * *

UNITED STATES PATENT AND TRADEMARK OFFICE
CERTIFICATE OF CORRECTION

PATENT NO. : 5,330,482
DATED : July 19, 1994
INVENTOR(S) : Rebecca C. Gibbs et al.

It is certified that error appears in the above-identified patent and that said Letters Patent is hereby corrected as shown below:

In column 3, line 5, please insert a period after "10".
In column 3, line 5, please change "in" to --In--.
In column 6, line 17, please change "monofiliment" to --monofilament--.
In column 6, line 25, please change "standard" to --stranded--.

Signed and Sealed this

Eighteenth Day of October, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO. : 5,330,482
DATED : July 19, 1994
INVENTOR(S) : Rebecca C. Gibbs et al.

It is certified that error appears in the above-indentified patent and that said Letters Patent is hereby corrected as shown below:

In column 2, line 56, please delete "0.055" and insert in lieu thereof --0.0055--.

In claim 9, line 4, please delete "0.0004" and insert in lieu thereof --0.004--.

In claim 18, line 4, please delete "0.0004" and insert in lieu thereof --0.004--.

Signed and Sealed this

Twenty-second Day of July, 1997

Attest:

BRUCE LEHMAN

Attesting Officer

Commissioner of Patents and Trademarks